United States Patent
Davis et al.

(10) Patent No.: US 8,089,630 B2
(45) Date of Patent: Jan. 3, 2012

(54) SPECTRAL NEAR-FIELD OPTICAL TOMOGRAPHY

(75) Inventors: Brynmor J. Davis, Champaign, IL (US); Jin Sun, Mountain View, CA (US); John C. Schotland, Merion, PA (US); Paul S. Carney, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 418 days.

(21) Appl. No.: 12/402,177

(22) Filed: Mar. 11, 2009

(65) Prior Publication Data

US 2009/0296094 A1 Dec. 3, 2009

Related U.S. Application Data

(60) Provisional application No. 61/036,518, filed on Mar. 14, 2008.

(51) Int. Cl.
*G01N 21/55* (2006.01)
(52) U.S. Cl. .......................................... 356/445; 356/448
(58) Field of Classification Search .......... 356/445–448, 356/601–613, 300–301, 303, 317–318; 702/167, 702/127, 155; 385/12–13, 43, 30, 32; 250/234, 250/200, 216
See application file for complete search history.

(56) References Cited

U.S. PATENT DOCUMENTS

| | | | |
|---|---|---|---|
| 2002/0154301 A1 | 10/2002 | Shen et al. ..................... | 356/301 |
| 2003/0039429 A1 | 2/2003 | Inoue et al. ..................... | 385/12 |
| 2006/0164638 A1 | 7/2006 | Narita ............................ | 356/318 |
| 2009/0276923 A1 | 11/2009 | Sumetsky ....................... | 850/32 |

OTHER PUBLICATIONS

Carney et al., "Near-Field Tomography," in Uhlmann (ed.), Inside Out: Inverse Problems and Applications, Cambridge University Press, pp. 131-168.
Carney et al., *Computational Lens for the Near Field*, Phys. Rev. Lett., vol. 92 No. 16, art. No. 163903 (2004).
Schmitt, *Optical Coherence Tomography (OCT): A Review*, IEEE J. Sel. Top. in Quant. Electronics, vol. 5 No. 4, p. 1205 (1999).
Sun et al., *Near-Field Scanning Optical Tomography: A Nondestructive Method for Three-Dimensional Nanoscale Imaging*, IEEE J. Sel Top. In Quant. Electronics, vol. 12, pp. 1072-1082, Nov./Dec. 2006.
Sun et al., *Strong tip effects in near-field scanning optical tomography*, Journal of Applied Physics, vol. 102, art. No. 103103 (2007).
Carney et al., *Inverse scattering for near-field microscopy*, Appl. Phys. Lett., vol. 77 No. 18, p. 2798 (Oct. 28, 2000).

*Primary Examiner* — Tri T Ton
(74) *Attorney, Agent, or Firm* — Sunstein Kann Murphy & Timbers LLP

(57) ABSTRACT

A method and computer program product for imaging an object are disclosed. The object is illuminated with an electromagnetic wave, characterized by a spectrum of illuminating wavevectors. Electromagnetic waves scattered by the object are detected, and are characterized by a spectrum of detected wavevectors. An aperture equal to or smaller than an instantaneous characterizing wavelength of the illuminating electromagnetic wave is disposed between the source and the detector. At least one of the illuminating and detected wavevectors is varied in magnitude to provide information regarding a scattering characteristic of the object. By applying a forward model of the aperture to derive a three-dimensional scattering model, a three-dimensional reconstruction of the object may be obtained by inverting a detected data function in terms of the forward model.

20 Claims, 8 Drawing Sheets

SPECTRAL NEAR-FIELD OPTICAL TOMOGRAPHY

CROSS-REFERENCE TO RELATED APPLICATIONS

This application claims priority to U.S. Provisional Application No. 61/036,518, filed Mar. 14, 2008.

STATEMENT REGARDING FEDERALLY SPONSORED RESEARCH OR DEVELOPMENT

This invention was developed with Government support under Grant Nos. F49620-03-10379 and FA9550-07-1-0096 awarded by the U.S. Air Force, and under Grant No. DMR 0425780 and CAREER Award Grant No. 239265, both awarded by the National Science Foundation. The Government has certain rights in the invention.

FIELD OF THE INVENTION

The present invention pertains to methods and apparatus for imaging in three dimensions with a resolution exceeding that corresponding to the wavelength of illuminating radiation.

DESCRIPTION OF RELATED ART

As used in this application and the accompanying claims, the following terms shall have the meanings indicated, unless the context otherwise requires:

Electromagnetic radiation, such as light, is characterized by one or more frequencies and propagation directions, collectively constituting a "spectrum" of wavevectors associated with the radiation.

An "aperture," as used herein and in any appended claims, is any geometrical configuration giving rise to diffraction of radiation. It is to be understood that the term aperture does not require an actual physical opening, and that a sharp metal tip, for example, or a sharpened facet of an optical fiber, may serve as a pointlike secondary source that illuminates a sample and serves the function of an aperture for purposes of the present treatment. Further discussion of this point may be found in Sun et al., *J. Appl. Phys.*, vol. 102, art. no. 103103 (2007), which is incorporated herein by reference in its entirety.

Unless the context otherwise requires, the term "near field," as used herein and in any appended claims, substantively or adjectivally, means a regime in which evanescent components of a scattering wavefunction are significant. Other regions of the field, more distant from the defining aperture, are referred to herein as the "far field."

In the nineteenth century, Ernst Abbe established that the resolving power of far-field optical imaging systems is subject to a diffraction limit since homogeneous waves (i.e., plane waves) propagating away from a scatterer contain only information corresponding to features greater than one half the wavelength of light. To overcome this limit and to infer structure at subwavelength scales, near-field techniques can be employed, such as those described in co-pending U.S. patent application Ser. No. 11/413,633, filed Apr. 28, 2006, which is incorporated herein by reference in its entirety. Near-field techniques use a small aperture that allows subwavelength structure to be resolved within the near field of the aperture.

While near-field instruments produce data sensitive to subwavelength-scale sample variations, it is difficult to establish a relationship between the data obtained and the physical properties of the sample. In the last decade, there has been significant progress both in the modeling of near-field imaging systems and in the subsequent interpretation of the data collected, as described, for example, by Carney et al., Phys. Rev. Lett., vol. 92, art. no. 163903 (2004), which is incorporated herein by reference in its entirety. In addition to allowing a quantitative understanding of the data collected by standard instruments, the modeling of near-field systems enables the application of computed imaging techniques. That is, new near-field modalities with multiplex data-to-sample relations can be paired with numerical processing to infer sample structure. Pertinent techniques are described in Carney & Schotland, "Near-Field Tomography," in Uhlmann (ed.), Inside Out: Inverse Problems and Applications, Cambridge University Press (2003), and in references therein, all incorporated herein by reference. The raw data need not provide an obvious representation of the spatial object structure.

Traditional near-field scanning optical microscopy (NSOM) systems collect data in two dimensions using probe scanning. U.S. Pat. No. 6,775,349 (Schotland & Carney) provides a description of such a system and is incorporated herein by reference in its entirety.

In many applications, however, two-dimensional imaging is less than optimal since important information is contained in the structure of the sample in the depth dimension. To image a three-dimensional sample from two-dimensional data, it is necessary to acquire additional data which, in near-field scanning optical tomography (NSOT), are then incorporated into the image using computed imaging techniques. For example, Gaikovich, Phys. Rev. Lett., vol. 98, art. no. 243901 183902 (2007), describes a microwave near-field tomography system where additional data are acquired by scanning the sample using probes of different sizes. Alternatively, additional near-field data may be collected using multiple observation angles, as described, for example, in Carney & Schotland (2003), op. cit.

At wavelengths such as optical wavelengths that are many orders of magnitude shorter than microwaves, the collection of data suitable for NSOT processing becomes increasingly difficult, as microwave techniques are generally inapplicable to this regime. Prior proposals called for the collection of multiple two-dimensional images which must be coregistered with subwavelength accuracy. In addition, most proposed NSOT systems required access to field measurements rather than intensity measurements. An interferometric instrument with nanoscale colocalization accuracy between the images collected is required to realize the collection of these data. Furthermore, the probe positioning equipment typically occupied a large solid angle above the sample, precluding a significant range of observation angles.

The principle of near-field inverse scattering has been experimentally demonstrated in a two dimensional imaging modality, as described by Carney et al. (2004). Moreover, Brehm et al., *Optics Express*, vol. 14, p. 11222, (2006), have recently reported an interferometric near-field system for two-dimensional imaging purposes that, additionally, probes the spectral response of the imaged sample. Both of these references are incorporated herein by reference in their entirety.

BRIEF SUMMARY OF THE INVENTION

Embodiments of the present invention improve upon the prior art by allowing reconstruction of a three-dimensional object's physical characteristics by varying the wavelength of illuminating radiation emanating from a single subwavelength aperture. Subwavelength spatial resolution of the sample may be obtained without using multiple probe tips, multiple observation angles, or subwavelength coregistration of multiple two-dimensional images.

In accordance with preferred embodiments of the present invention, a method is provided for imaging an object. The method has steps of:

a. illuminating the object with an illuminating electromagnetic wave via an illumination path, wherein the illuminating electromagnetic wave is characterized by a spectrum of illuminating wavevectors;

b. detecting electromagnetic waves scattered by the object via a collection path, wherein the detector is characterized by a spectrum of detected wavevectors; wherein an aperture, disposed within at least one of the illuminating path and collection path, is equal to, or smaller than, an instantaneous characterizing wavelength of the electromagnetic wave; and c. varying the magnitude of at least one of the illuminating wavevectors and detected wavevectors in such a manner as to provide information regarding a scattering characteristic of the object.

In accordance with other embodiments of the invention, the information provided regarding a scattering characteristic of the object may be, specifically, in a direction along the illuminating path. The step of detecting may include disposing the detector in a far field, and the aperture may be a tip or other physical structure.

In yet further embodiments of the invention, the method for imaging an object may include further steps of:

d. applying a forward model of the imaging system in a manner as to derive a three-dimensional scattering model; and e. inverting a detected data function in terms of the forward model to obtain a three-dimensional reconstruction of the object.

The forward model may be expressed in terms of a block-diagonalized forward integral equation, for example. The step of illuminating the object may include illumination by means of a broadband source, and the broadband source may be a pulsed laser. The step of illuminating the object may also include scanning a wavelength of a substantially monochromatic source.

In further embodiments still, the method may also have steps of varying observing angles and of scanning the aperture to a plurality of positions in a plane substantially parallel to the surface of the object. Scanning the aperture may include scanning a position of a probe tip that is small on a scale of the characterizing wavelength of the illuminating electromagnetic wave. The method for imaging may also have a step of spectrally dispersing electromagnetic waves scattered by the object prior to detection by the detector. Moreover, detection of electromagnetic waves scattered by the object may specifically include detecting a phase of the scattered electromagnetic waves.

In accordance with another aspect of the present invention, a computer program product is provided for deriving an image of a physical object. The computer program product has a computer usable medium with:

a. program code for generating a forward scattering model that includes variation of a magnitude of an illuminating wavevector and interposition of an aperture in an illuminating path or a collection path;

b. program code for receiving a signal based on detection of scattering from the physical object; and c. program code for deriving a scattering characteristic of the physical object based on comparison with the forward scattering model of detected scattering from the object.

Moreover, the computer program product may also have:

d. program code for applying a forward model of the imaging system in a manner as to derive a three-dimensional scattering model; and e. program code for inverting a detected data function in terms of the forward model to obtain a three-dimensional reconstruction of the object.

In another embodiment, an apparatus is provided. The apparatus has an illumination source for illuminating the object with an illuminating electromagnetic wave via an illumination path, the illuminating electromagnetic wave being characterized by a spectrum of illuminating wavevectors. The apparatus also has a detector for detecting electromagnetic waves scattered by the object along a collection path, the scattered electromagnetic waves being characterized by a spectrum of detected wavevectors. The apparatus further has an aperature equal to or smaller than an instantaneous characterizing wavelength of an illuminating wavevector or a detected wavevector, the aperature being disposed within at least one of the illuminating path and the collection path. And the apparatus has a processor capable of applying a forward model of the imaging system to derive a three-dimensional scattering model and inverting a detected data function in terms of the forward model to obtain a three-dimensional reconstruction of the object. In related embodiments, the illumination source is a broadband source, such as a pulsed laser, the laser being tunable to vary the illuminating wavevectors. The processor may be capable of controlling the laser in addition to its other processing capabilities.

BRIEF DESCRIPTION OF THE DRAWINGS

The foregoing features of the invention will be more readily understood by reference to the following detailed description, taken with reference to the accompanying drawings, in which:

FIGS. 3(f-j) show reconstructions for single-angle broadband NSOT systems, while FIGS. 3(k-o) show reconstructions for two-angle broadband NSOT systems. FIGS. 3(a), 3(f) and 3(k) show the x-z plane while the remaining plots give x-y detail. The axes used for FIG. 3(a-e) are repeated in FIGS. 3(f-j) and FIGS. 3(k-o);

DETAILED DESCRIPTION OF SPECIFIC EMBODIMENTS OF THE INVENTION

Near-field scanning optical tomography (NSOT), an extension of NSOM, amounts to inverting the data collected by NSOM and reconstructing the sample, instead of taking the raw data as an image of the sample. In accordance with preferred embodiments of the present invention, a novel NSOT modality is described. Rather than using multiple observation angles or multiple probes, data are collected in a third dimension by using the spectral degree of freedom. The idea of constructing an image in N spatial dimensions by collecting data in (N−1) spatial dimensions and a spectral dimension has found application in conventional far-field techniques such as optical coherence tomography, described by Schmitt, *IEEE J. Sel. Top. in Quant. Electronics*, vol. 5, p. 1205, (1999) and synthetic aperture radar, described by Curlander et al., *Synthetic Aperture Radar: Systems and Signal Processing*, Wiley Interscience, (1991). Multiple images corresponding to different wavelengths can be collected from each probe scan and are therefore inherently coregistered.

In the following generalized treatment of broadband NSOT systems, two frame-works are employed: one, a scalar treatment, in which is the sample is represented by a nondispersive scattering potential V(r) with a background of free space, and a vector treatment, in which a more physical vector susceptibility $\eta(r)$ is used to characterize the sample. Following the monochromatic treatment given in Carney et al., *Applied Physics Letters*, vol. 77, p. 2798, (2000), which is incorporated herein by reference in its entirety, an instrument model is developed, an inversion formula based on the singular value decomposition (SVD) is derived, and simulations are used to determine the expected system performance.

Forward Model

Figure 1:
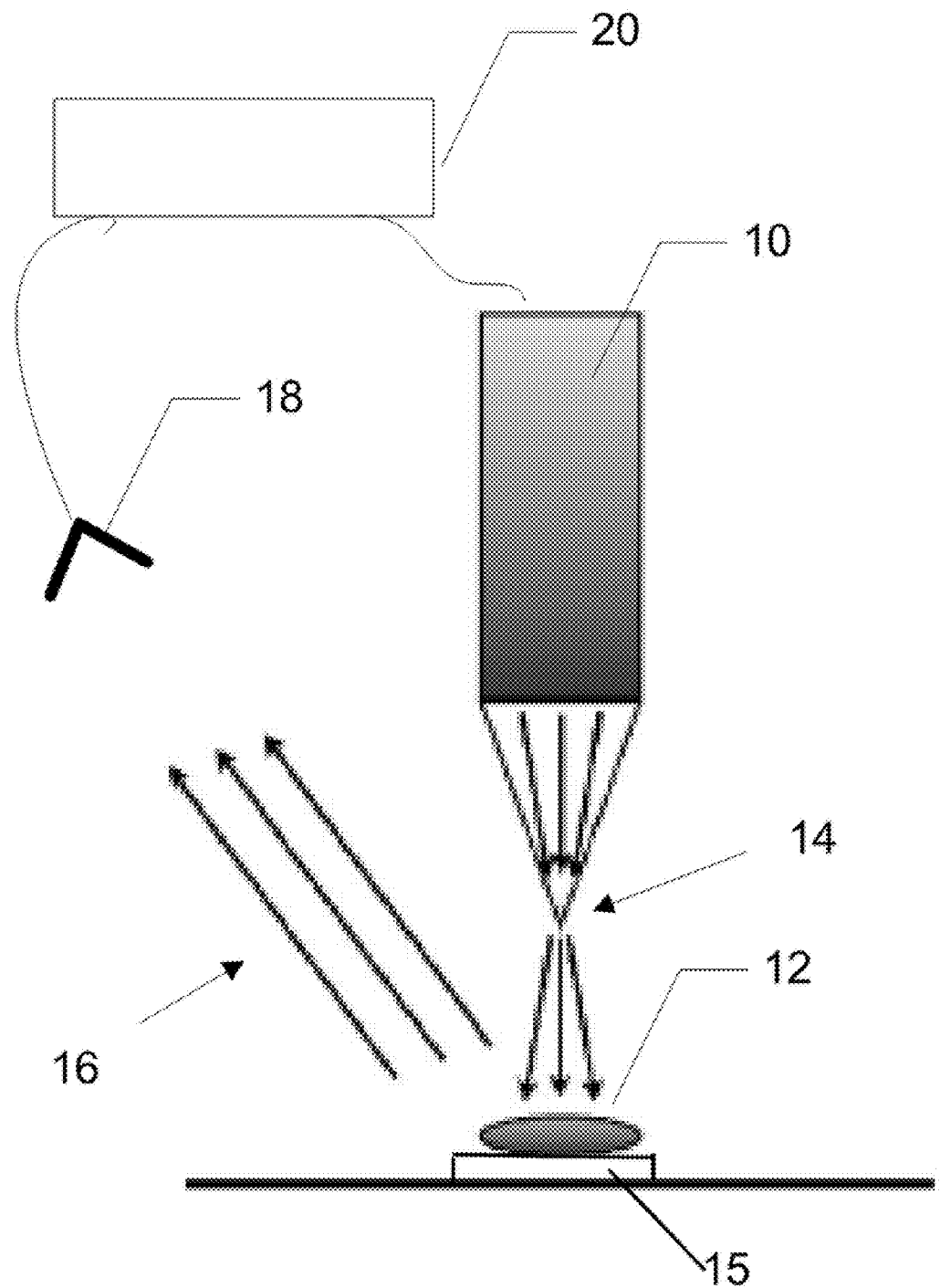
FIG. 1 is a schematic depiction of an implementation of a sub-wavelength near-field imaging system in accordance with an embodiment of the present invention.
Figure 2:
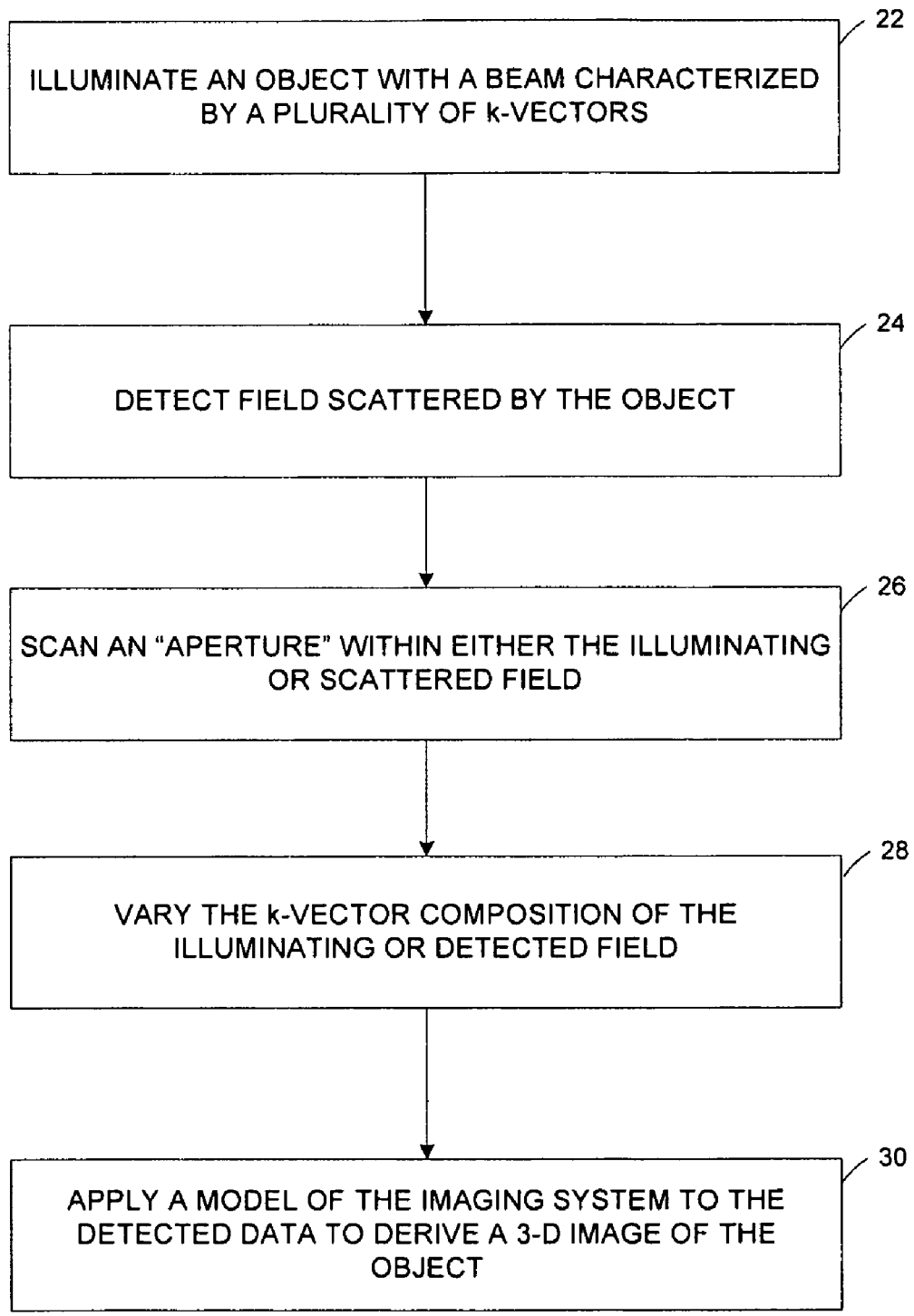
FIG. 2 is a flow chart depicting process steps for sub-wavelength imaging in accordance with embodiments of the present invention.

In the following description of embodiments of the present invention, the NSOT probe is assumed to behave as a point source illuminating the sample. Referring to FIGS. 1 and 2, light of an illumination source 10 illuminates object 12 in process 22. Illumination source 10 may emit a narrow band of wavelengths that are varied or tuned. A tunable laser serves such a purpose. In accordance with some embodiments, source 10 may be a broadband source, which may further include passive or active spectral filtering. Object 12 is located in the near field of an aperture 14, which may be an actual opening or a probe region, small on the scale of the pertinent wavelength, from which the incident beam is reflected or scattered. Aperture 14 is situated such that object 12 lies within the near field of light emanating from the aperture. In process 24, light 16 scattered from the object is detected by one or more detectors 18 disposed in the far field with respect to the light from aperture 14 that is scattered by object 12. In process 26, the position of aperture 14 relative to the surface of object 12 is scanned in a direction that is locally substantially parallel to the surface of object 12, such that the illumination intercepts successive regions of the object. For example, the scan may be accomplished using a scanner 15. The scanner may be any positioner or actuator known in the art to be useful for this purpose. The spectrum of the illuminating light, which may be narrow-band or broadband, within the scope of the present invention, may also be varied as a function of time, in process 28. Controller 20, which may include a computer processor, governs operation of source 10, scanning the wavelength of the source, and receives a signal from detector 18 for processing, as described herein. The resulting scattered light is then collected coherently as a function of angle and/or wavelength depending on the NSOT modality considered. In process 30, a forward scattering model is applied to the gathered data, as described in the following.

The following paradigm is employed in the description. A weakly scattering sample, described by the dielectric susceptibility $\eta(r)$, is placed in vacuum above a half-space with a uniform index of refraction n. The interface is assumed to coincide with the z=0 plane. An apertureless tip has an effective polarizability $\alpha_e$, which depends on the height of the tip above the z=0 plane, as defined in Sun et al. (2007). While the development of a forward scattering model is described in terms of an apertureless tip for heuristic convenience, it is to be understood that the scope of the invention is not so limited. The tip 14 is scanned over the sample while the system is illuminated by an incident plane wave $E^i$. The incident wave is characterized by a free-space wave vector $-k_d=-[q_d,k_z(k_d,k)]$, where the notation refers to the transverse component q of the wavevector and the projection $k_z$ of the wavevector in the z direction. $|-k_d|=k$, and the polarization, p, is given by $$E^i(r,k_d)=[I+\mathcal{R}(-q_d,k)e^{2ik_z(q_d,k)z}]e^{iq_d\cdot\rho-ik_z(q_d,k)z}p \quad (1)$$

where $\mathcal{R}$ is the reflection tensor at the half-space interface, as given, again, by Sun et al. (2007). Specifically, the projection of the wave vector onto the z axis is given by $$k_z(q,k)=\begin{cases}\sqrt{k^2-q^2} & q^2 \leq k^2 \\ i\sqrt{q^2-k^2} & q^2 > k^2.\end{cases} \quad (2)$$

In a scalar analysis, where the resulting scattered light is collected coherently as a function of angle, the scattered field, in a first Born (i.e., single scattering) approximation, can be expressed as $$U(r,r_d,k)=\int d^3r' G(r,r',k)G(r',r_d,k)V(r'), \quad (3)$$

where r is the position of the probe, r' is a dummy variable describing the scattering position within the sample, $r_d$ is the detector position, k is the wavenumber and the Green's function is $G(r,r',k)=e^{ik|r'-r|}/|r'-r|$. Eq. (3) describes light originating from a point source at r, scattering from all sample positions r' and propagating to $r_d$. Here the NSOT system is described in illumination mode but the theory may be equally applied to detection mode, within the scope of the present invention, by considering a source at $r_d$ and a point detector at r. It is also implicit that the probe does not strongly interact with the sample—an approximation investigated in Sun et al., (2007).

The second Green's function in Eq. (3) is simplified as $G(r',r_d,k) \approx e^{-ik\cdot r'}e^{ikr_d}/r_d$, since $r_d$ is in the far-field. Note that k and $r_d$ determine the detection wavevector k and that this approximation assumes r' is near the origin. Collecting the angular and spectral dependence of U in k and dropping dependence on $r_d$ (the constant distance to a detection hemisphere) gives $$U(r,k)=\int d^3r' G(r,r',k)e^{-ik\cdot r'}V(r'). \quad (4)$$

It is now convenient to express the remaining Green's function using the Weyl representation, as:

$$G(r,r',k)=\frac{i}{2\pi}\int\frac{d^2q}{k_z(q,k)}\exp[iq\cdot(\rho-\rho')+ik_z(q,k)|z-z'|], \quad (5)$$

where $r=(\rho,z)$ and $k_z(q,k)=\sqrt{k^2-q^2}$ (with the principal branch used to evaluate this square root).

It is assumed that the probe-scan plane is fixed above the sample and is set to z=0. The definition $Q(q,k)=[q,k_z(q,k)]$ is used so that the data are written as, $$U(\rho, k) = \frac{i}{2\pi} \int \frac{d^2 q e^{iq \cdot \rho}}{k_z(q,k)} \int d^3 r' e^{-i[k+Q(q,k)] \cdot r'} V(r'). \quad (6)$$

Taking the transform with respect to the scan dimensions $\rho$, $$\tilde{U}(q, k) = \frac{2\pi i}{k_z(q,k)} \int d^3 r' e^{-i[k+Q(q,k)] \cdot r'} V(r'), \quad (7)$$

where represents a transverse Fourier transform. The transverse Fourier transform contained in the remaining integral can also be evaluated by defining $\hat{V}$, the two-dimensional transverse Fourier transform of V. The observation model now simplifies to a one-dimensional integral equation, $$\tilde{U}(q, k) = \frac{2\pi i}{k_z(q,k)} \int dz' e^{-i[k_z(k_\parallel,k)+k_z(q,k)]z'} \tilde{V}(k_\parallel + q, z'), \quad (8)$$

where $k=[k_\parallel, k_z(k_\parallel, k)]$. This model applies to multi-angle and/or broadband NSOM. The dependence on both angle and wavelength is contained in k.

The Fourier-domain model expressed in Eq. (8) implicitly assumes an infinite and continuous scan range, as the continuous, infinite-limit Fourier transform is employed in the derivation. A finite and discrete sampling grid approximates Eq. (8), provided that the probe scanning step is sufficiently small to preclude aliasing and the scan range covers all significant signal.

In a vector analysis, the polarization p of the back-scattered field is assumed to be measured at $r_d$ ($\rho_d, z_d$), which is in the same direction as $k_d$, and the first Born term is given by $$E_s = p \cdot [TS + ST] \cdot E^i, \quad (9)$$

where T and S represent integral operators mapping a field incident on the tip or the sample to the respective scattered field. They are given by $$[S \cdot E](r) = k^2 \int d^3 r' G(r,r',k) \eta(r') E(r'), \quad (10)$$

and $$[T \cdot E](r) = k^2 \int d^3 r' G(r,r',k) \alpha_e \delta(r'-r_t) E(r'), \quad (11)$$

where $r_t = (\rho_t, z_t)$ is the position of the tip, G is the half-space Green's tensor, and $\alpha_e$ is the polarizability used in the point model of the tip. It may be noted that while the scattering from the tip is exactly described by T, the scattering from the sample, described by S, is of first-Born type.

In this vector case, the Green's tensor is conveniently expressed in a plane wave decomposition as $$G(r, r', k) = \frac{i}{2\pi} \int d^2 q g(z, z', k; q) \exp[iq \cdot (\rho - \rho')], \quad (12)$$

where $g(z,z';q)$, the plane wave component, is given by $$g(z, z', k; q) = \quad (13)$$
$$\frac{1}{k_z(q,k)} \begin{cases} [\mathcal{D}(q) e^{ik_z(q,k)(z-z')} + \mathcal{R}(q) e^{ik_z(q,k)(z+z')}] & 0 \le z' \le z \\ [\tilde{\mathcal{D}}(q) e^{ik_z(q,k)(z'-z)} + \mathcal{R}(q,k) e^{ik_z(q)(z'+z)}] & 0 \le z < z', \end{cases}$$

where dependence on the wave number k of the polarization tensors $\mathcal{D}(q)$ and $\tilde{\mathcal{D}}(q)$, the reflection tensor $\mathcal{R}(q)$ and the transmission tensors $\mathcal{T}(q)$ and $\mathcal{T}'(q)$, as given in Sun et al. (2007), is understood. The Green's tensor has the asymptotic form $$G(r_d, r', k_d) = \frac{e^{ikr_d}}{r_d} e^{-ik_d \cdot r'} [\mathcal{D}(q_d) + R(q_d) e^{2ik_z(q_d,k)z'}] \quad (14)$$

with the observation point $r_d$ in the far field in the upper half space and the source point r' near the origin in the upper half space. Making use of Eqs (10), (11), (14), it is seen that the scattered field given by Eq. (9) can be represented by the scattering amplitude $A = A_{TS} + A_{ST}$, i.e., $$E_s(r_d, r_t, k_d) = \frac{e^{ikr_d}}{r_d} A(r_t, k_d), \quad (15)$$

where $$A_{TS}(r_t, k_d) = k^4 \int d^3 r' e^{-ik_d \cdot (r_t + r')} p \cdot [\mathcal{D}(q_d) + \mathcal{R}(q_d) e^{2ik_z(q_d,k)z_t}] \quad (16)$$
$$\alpha_e G(r_t, r', k) \times [I + \mathcal{R}(-q_d) e^{2ik_z(q_d,k)z'}] p \eta(r'),$$

$$A_{ST}(r_t, k_d) = \quad (17)$$
$$k^4 \int d^3 r' e^{-ik_d \cdot (r' + r_t)} p \cdot [\mathcal{D}(q_d) + \mathcal{R}(q_d) e^{2ik_z(q_d,k)z'}] G(r', r_t, k)$$
$$\alpha_e \times [I + \mathcal{R}(-q_d) e^{2ik_z(q_d,k)z_t}] p \eta(r').$$

Note that p represents certain TEM polarization in the propagation direction defined by $k_d$, and therefore lies in the invariant subspace of the polarization operator $\mathcal{D}(q_d)$, which implies that $$p \cdot \mathcal{D}(q_d) = p. \quad (18)$$

Assuming that $\alpha_e$ is a symmetric tensor, i.e., $\alpha_e = \alpha_e^T$ where superscript T represents matrix transpose, and considering the relationships (described in Sun et al. (2007))

$$\mathcal{R}(-q_d) = \mathcal{R}^T(q_d) \quad (19)$$

and $$G(r', r_t, k) = G^T(r_t, r', k), \quad (20)$$

it may be seen that $A_{ST} = A_T{}^T{}_S = A_{TS}$ since $A_{TS}$ is a scalar quantity. Hence the scattered field may be represented by its amplitude $A(r_t, k_d) = 2 A_{TS}(r_t, k_d)$.

Following the procedures outlined in Sun et al. (2007), the data function $\Phi$ is defined as the lattice Fourier transform of $A(r_t, k_d) = 2 A_{TS}(r_t, k_d)$ with respect to $\rho_t$ with lattice spacing h, $$\Phi(q_t, z_t, k_d) = h^2 \sum_{\rho_t} A(r_t, k_d) e^{-iq_t \cdot \rho_t}, \quad (21)$$

where the sum over $\rho_t$ is carried out over all lattice vectors and $q_t$ belongs to the first Brillouin zone (FBZ) of the lattice. In this case FBZ=$[-\pi/h, \pi/h] \times [-\pi/h, \pi/h]$. By substituting Eq. (16) into Eq. (21) and making use of the plane wave representation of the Green's tensor (12), and the identity $$\sum_{\rho} e^{iq \cdot \rho} = \left(\frac{2\pi}{h}\right)^2 \sum_{q''} \delta(q - q''), \quad (22)$$

where q" denotes a reciprocal lattice vector, the data function is expressed as $$\Phi(q_t, z_t, k_d) = k_z^{-1}(q_d + q_t, k) \int dz' L(q_t, z_t, k_d, z') \tilde{\eta}(2q_d + q_t, z'), \quad (23)$$

where, $\tilde{\eta}(q, z') = \int d^2\rho' \eta(\rho', z') e^{-iq \cdot \rho'}$ is the lateral Fourier transform of the sample function $\eta$, assumed to be band-limited to the FBZ, and the kernel of integration L is given by $$L(q_t, z_t, k_d, z') = \quad (24)$$
$$4\pi i k^4 e^{i[k_z(q_d + q_t, k) - k_z(q_d, k)]z_t} p \cdot [\mathcal{D}(q_d) + \mathcal{R}(q_d) e^{2ik_z(q_d, k)z_t}] \times$$
$$\alpha_e [\mathcal{D}(q_d + q_t) e^{-ik_z(q_d + q_t, k)z'} + \mathcal{R}(q_d + q_t) e^{ik_z(q_d + q_t, k)z'}] \times$$
$$[I e^{-ik_z(q_d, k)z'} + \mathcal{R}(-q_d) e^{ik_z(q_d, k)z'}] p.$$

Equation (23) is the block-diagonalized forward integral equation, and is more suitable for a numerical inversion than Eq. (16).

Inversion

In the scalar case, while the model given in Eq. (3) could be used in the design of an inversion process, Eq. (8) is much more appealing as it is only a one-dimensional integral equation. The transverse component of the data collection is linear and shift-invariant and is therefore diagonalized in the Fourier-domain, reducing the dimensionality of the problem. Regarding the transverse Fourier-transform variables q as parameters, the model can be rewritten, $$\tilde{\mathcal{U}}_q(k) = [A_q \tilde{V}_q](k) \quad (25)$$
$$= \int dz e^{-i[k_z(k_\parallel, k) + k_z(q - k_\parallel, k)]z} \tilde{V}_q(z),$$

where $\tilde{\mathcal{U}}_q(k) = k_z(q - k_\parallel, k) \tilde{U}(q - k_\parallel, k)/(2\pi i)$. The operator kernel is $$A_q(k, z) = e^{i[k_z*(k_\parallel, k) + k_z*(q - k_\parallel, k)]z}, \quad (26)$$

with $[A_q u](k) = \langle A_q(k, z), u(z) \rangle_z$, and angle brackets denoting an inner-product. In z space, the inner-product is $\langle s(z), u(z) \rangle_z = \int dz\, s^*(z) u(z)$. The adjoint operator is $A_q^\dagger$, with $[A_q^\dagger w](z) = \langle A_q^*(k, z), w(k) \rangle_k$ and the k-space inner-product may be written as $\langle v(k), w(k) \rangle_k = \Sigma_k v^*(k) w(k)$. The operator $A_q$ maps a continuous function on z to data collected on a discrete set $\kappa$ of k vectors. The SVD analysis of such semi-discrete systems is standard and will be used, without limitation and for purposes of the current description, to invert the mapping from z to $\kappa$.

The Gram matrix for $A_q$ defines a normal operator $\langle M_q(k, k'), \cdot \rangle_{k'}$ which effects a matrix multiplication in k space. The Gram matrix is $$M_q(k, k') = \langle A_q(k, z), A_q(k', z) \rangle_z, \quad (27)$$
$$= \begin{cases} \left.\frac{\exp[-iQ(q, k, k')z]}{-iQ(q, k, k')}\right|_{z_{min}}^{z_{max}}, & Q(q, k, k') \neq 0, \\ z_{max} - z_{min}, & Q(q, k, k') = 0, \end{cases}$$

where k and k' index the rows and columns respectively, $Q(q, k, k') = k_z(k_\parallel, k) - k_z^*(k'_\parallel, k') + k_z(q - k_\parallel, k) - k_z^*(q - k'_\parallel, k')$, and $z_{min}$ and $z_{max}$ giving the longitudinal boundaries of the sample. Matrix multiplication by $M_q$ is a mapping from $\kappa$ to $\kappa$ and represents the normal operator for this system. Note that the Gram matrix is Hermitian and nonnegative definite.

The real nonnegative eigenvalues of $M_q$ and the corresponding eigenvectors are found numerically. The $l^{th}$ eigenvector $c_q^l(k)$ (where the measurement wavevector k indexes the vector element) is the $l^{th}$ left-singular vector of $A_q$, and the square root of the $l^{th}$ eigenvalue of $M_q$ is the singular value $\sigma_q^l$. The $l^{th}$ right singular vector can then be calculated as, $$\psi_q^l(z) = [A_q^\dagger c_q^l](z) = \langle A_q^*(k, z), c_q^l(k) \rangle_k. \quad (28)$$

This defines the SVD, so $\tilde{\mathcal{U}}_q(k)$ can be expressed as $$[A_q \tilde{V}_q](k) = \sum_{l=1}^N \sigma_q^l c_q^l(k) \langle \psi_q^l(z), \tilde{V}_q(z) \rangle_z, \quad (29)$$

where N is the number of elements in $\kappa$.

The preprocessed data $\tilde{\mathcal{U}}_q$ can then be used in the inversion of Eq. (25). The truncated singular value decomposition (TSVD) is employed to find $\tilde{V}_q^+(z)$, an estimate of the sample in q-z space. The TSVD is used to provide stability to noise and is expressed as $$\tilde{V}_q^+(z) = \sum_{l=1}^{N^+} \frac{1}{\sigma_q^l} \psi_q^l(z) \langle c_q^l(k), \tilde{U}_q(k) \rangle_k, \quad (30)$$

where $N^+$ is the number of singular components d in the reconstruction. The regularization of the inverse problem is controlled by $N^+$—a greater $N^+$ gives better reconstruction fidelity while a lesser $N^+$ reduces sensitivity to measurement noise.

Figure 3:
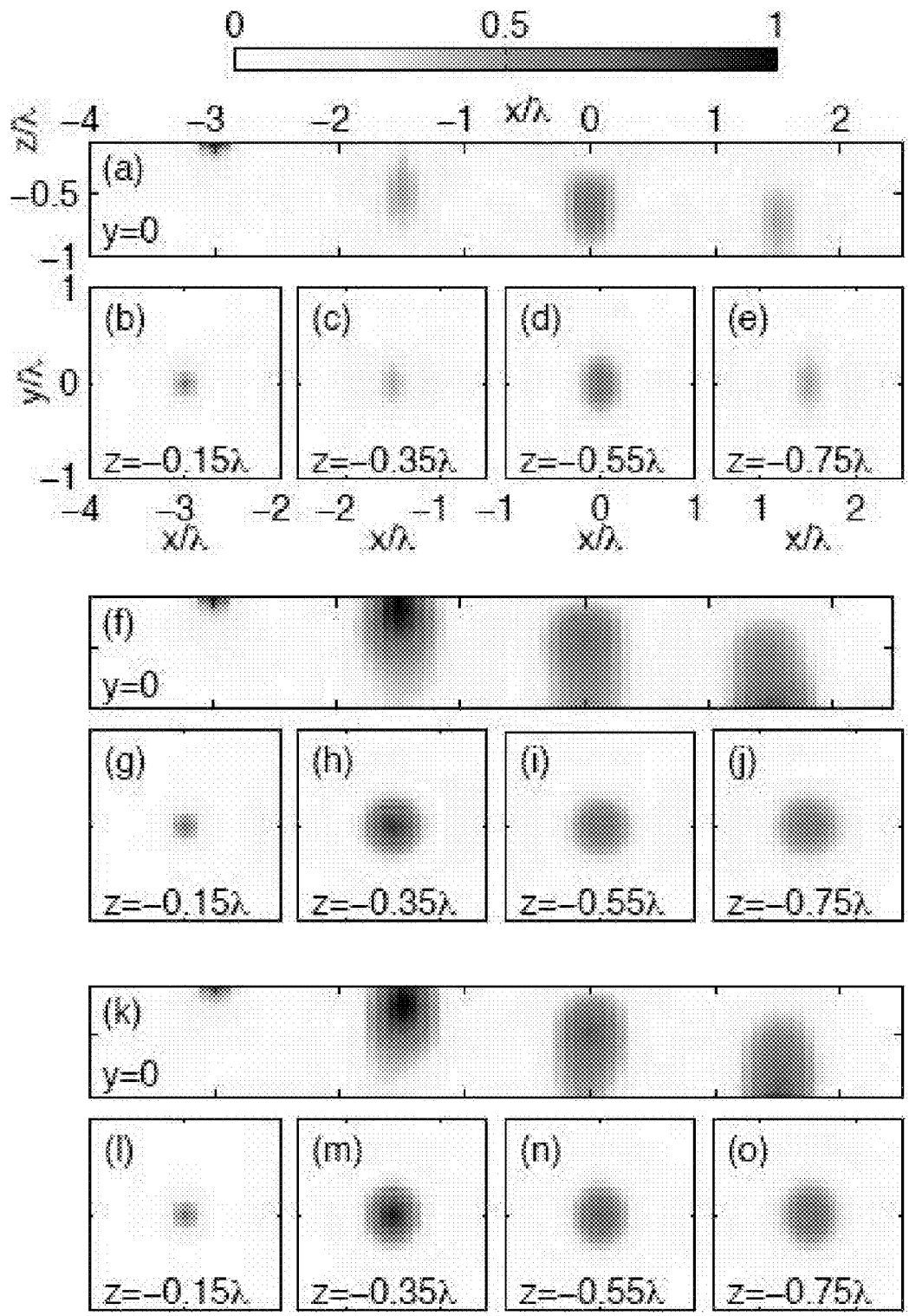
FIGS. 3(a-e) represent reconstructions for the many-angle NSOT systems, but at a solitary wavelength λ. The other simulations of FIG. 3 correspond to broadband reconstructions in accordance with embodiments of the present invention.

Referring now to FIG. 3, the performance of the broadband and/or multi-angle NSOT systems was investigated using numerical simulations and the scalar forward model and inversion paradigms. Synthetic data were generated by defining a test sample V(r) and evaluating Eq. (3) for the modality considered. In this case the sample consisted of four point scatterers at $(-3, 0, -0.15)\lambda$, $(-1.5, 0, -0.35)\lambda$, $(0, 0, -0.55)\lambda$ and $(1.5, 0, -0.75)\lambda$, where $\lambda$ is a nominal wavelength. The first scatterer had a scattering potential 80% lower than the other scatterers in order to give a reconstruction with comparable peak amplitudes. For the purposes of reconstruction, the sample is assumed to lie in the region $-\lambda < z < -0.1\lambda$.

Three NSOT systems were considered: the first is a single wavelength ($\lambda$), many-angle system, as discussed in Carney et al. (2000), with k lying in the x-z plane and having 32 observation angles evenly spaced across a semicircle; the second system has a single observation angle (k lies in the x-z plane at 45° from vertical) and 32 observation wavelengths between 0.8λ and 1.2λ; and the third system has the same spectral range as the second but with two observation angles (30° and 60° from vertical in the x-y plane) and 16 spectral samples per observation angle. All three systems have a scan step of λ/12 in both x and y, with 100 and 80 samples in the x and y directions respectively.

The synthetic data were inverted according to Eq. (30), with $N^+$ chosen so that any singular components with singular value less than one one-hundredth of the maximum were discarded. This criterion corresponds to a signal to noise ratio of approximately 40 dB. The magnitudes of the resulting reconstructions are shown in FIG. 3, where each reconstruction (one for each system) has been normalized by its maximum value.

From FIG. 3 it can be seen that the resolution for the broadband (FIGS. 3(a-e)) and limited observation angle (FIGS. 3(f-j)) NSOT systems is poorer than for the many-angle case, but meaningful three-dimensional detail is given. In all systems the resolution degrades with depth into the sample. Due to asymmetry in the observation angles, the many-angle and two-angle NSOT systems have differing resolutions in the x and y directions.

The inversion of Eq. (23) is very much similar to that outlined in Sun et al., *IEEE Journ. Sel. Top. Quant. Electronics*, vol. 12, p. 1072, (2006), incorporated herein by reference in its entirety, and Sun et al. (2007).

By observation, the integral kernel L in Eq. (24) may be written in the form of a separation of variables $$L_Q(k_d, z) = \sum_{j=1}^{4} C_Q^{(j)}(k_d) e^{-i\lambda_Q^{(j)}(k_d)z}, \quad (31)$$

where subscript q denotes collectively the parameters ($z_t$, $2q_d+q_t$), which are held as constants during the reconstruction of one component of $\tilde{\eta}$, i.e., $\tilde{\eta}(2q_d+q_t,z) \equiv \tilde{\eta}_Q(z)$. The coefficients $C_Q^{(j)}$ and $\lambda_Q^{(j)}$ are given by $$\left.\begin{array}{l}C_Q^{(1)}(k_d) = p \cdot \mathcal{D}(q_d + q_t) \\ C_Q^{(2)}(k_d) = p \cdot \mathcal{R}(q_d)\mathcal{D}(q_d + q_t) \\ C_Q^{(3)}(k_d) = p \cdot \mathcal{R}(-q_d - q_t) \\ C_Q^{(4)}(k_d) = p \cdot \mathcal{R}(q_d)\mathcal{R}(-q_d - q_t)\end{array}\right\} \cdot 4\pi i k^4 \alpha_e \times \quad (32)$$

$$[I + \mathcal{R}(-q_d)e^{2ik_z(q_d,k)z_t}]pe^{i[k_z(q_d+q_t,k)-k_z(q_d,k)]z_t}$$

and $$\lambda_Q^{(1)}(k_d) = k_z(q_d, k) + k_z(q_d + q_t, k), \quad (33)$$

$$\lambda_Q^{(2)}(k_d) = -k_z(q_d, k) + k_z(q_d + q_t, k),$$

$$\lambda_Q^{(3)}(k_d) = k_z(q_d, k) - k_z(q_d + q_t, k),$$

$$\lambda_Q^{(4)}(k_d) = -k_z(q_d, k) - k_z(q_d + q_t, k).$$

The Gram matrix $M_Q(k_d, k'_d)$, defined as $$M_q(k_d, k'_d) = \int dz L_q(k_d, z) L_Q^*(k'_d, z), \quad (34)$$

where the integral is carried over an interval in which the sample function is supported, is found to be $$M_Q(k_d, k'_d) = \sum_{j,l=1}^{4} C_Q^{(j)}(k_d) C_Q^{(l)}(k'_d)^* \frac{\exp\left\{i\left[\lambda_Q^{(l)}(k'_d)^* - \lambda_Q^{(j)}(k_d)\right]z_{max}\right\} - 1}{i[\lambda_Q^{(l)}(k'_d)^* - \lambda_Q^{(j)}(k_d)]}, \quad (35)$$

where $z_{max}$ is the maximum height of the sample, and the singularities at points where denominator is zero are of removable type. A regularized solution is thus given by $$\tilde{\eta}_Q^+(z) = \sum_{k_d, k'_d} L_Q^*(z, k_d) M_Q^+(k_d, k'_d) \tilde{\Phi}_Q(k'_d), \quad (36)$$

where $M_Q^+$ is the regularized pseudo-inverse of the Gram matrix, and $$\tilde{\Phi}_Q(k'_d) = k_z(q'_d + q_t, k) \Phi(q'_d, z_t, k'_d) \quad (37)$$

is the pre-processed data. Regularization of the Gram matrix inversion may be trivially modified to achieve same effects as regularizing inversion of the forward operator. The corresponding object reconstruction may be obtained through a two-dimensional inverse Fourier transform, usually realized by a fast Fourier transform (FFT) algorithm.

Figure 4:
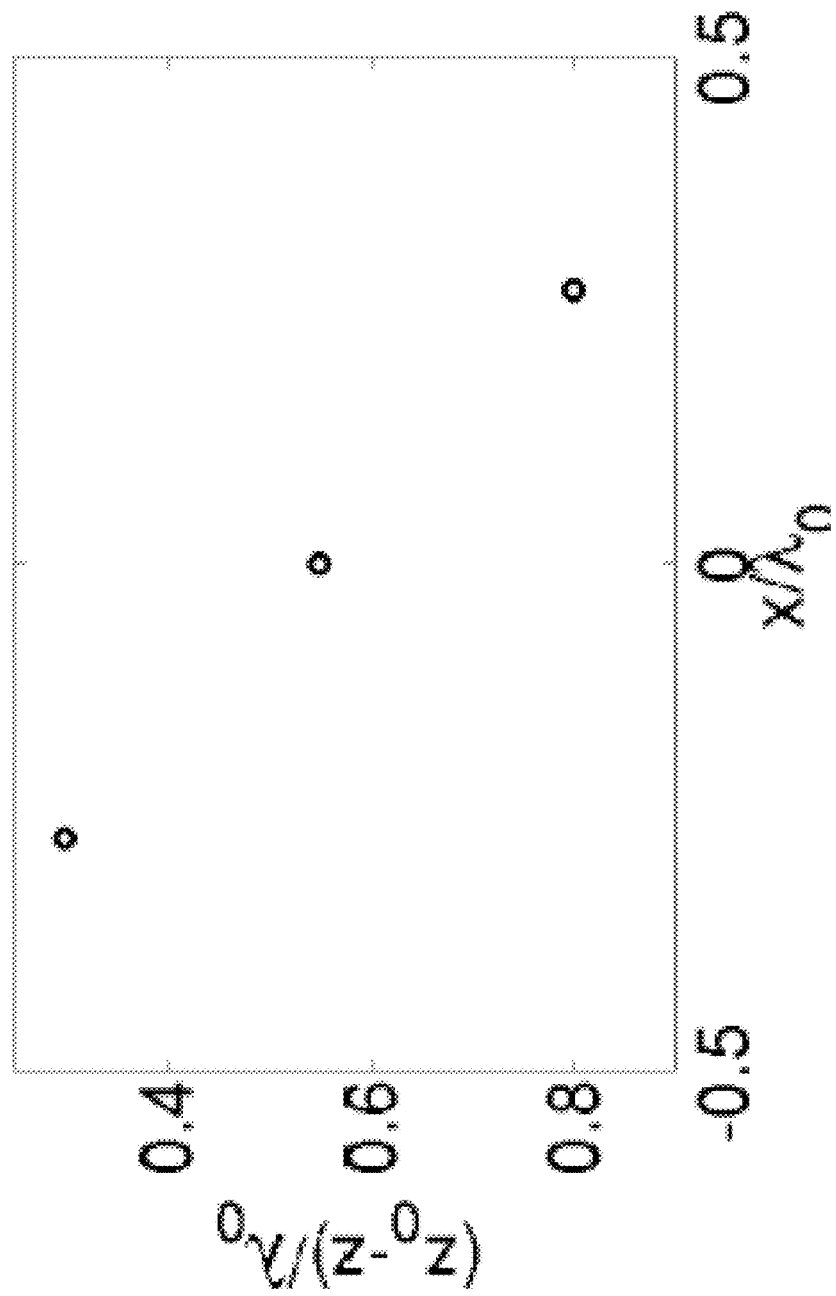
FIG. 4 is a sample object used in the simulation of FIGS. 5(a-b) and 6(a-b), with the vertical axis representing distance from the scan plane in the z direction.

The foregoing procedures are illustrated in a series of numerical simulations, in which scattering data from a sample, depicted in FIG. 4, that consists of three point-like scatterers on top of a half space, below the scan plane $z_0 = \lambda_0$, where $\lambda_0$ is the minimal free-space wavelength, is simulated. The illuminations are transverse-magnetic (TM) polarized spectroscopic plane waves with different angles of incidence. The forward simulations are consistent with the forward model described above, i.e., a weakly scattering sample is assumed, and the scattering data are collected in the entire measurement plane without truncation or windowing. The tip scan spacing $h = \lambda/16$, and the sampling rate in the frequency domain (spectroscopic sampling) is $k_0/100$, where $k_0$ is the maximal spatial frequency, and $k_0 = 2\pi/\lambda_0$.

Figure 5A:
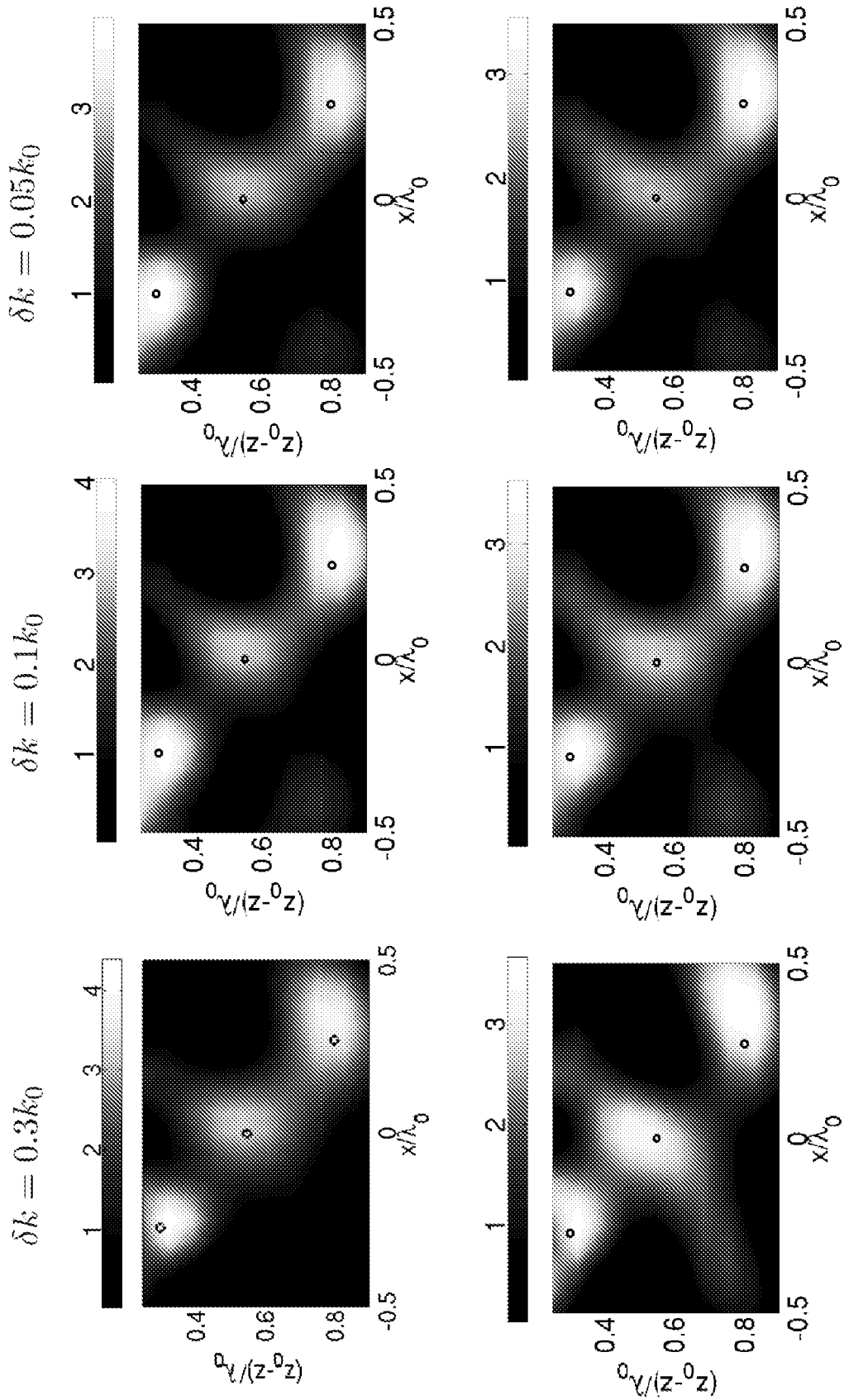
FIGS. 5(a-b) show tomographic reconstructions of the sample under different numbers of incident angles and bandwidth; $\delta k$ is the bandwidth in the spatial frequency of the incident field; $N_i$ is the number of angles of incidence, which were spaced in such a way that projections of the incident wave vectors onto the normal (z) direction of the interface do not overlap.
Figure 5B:
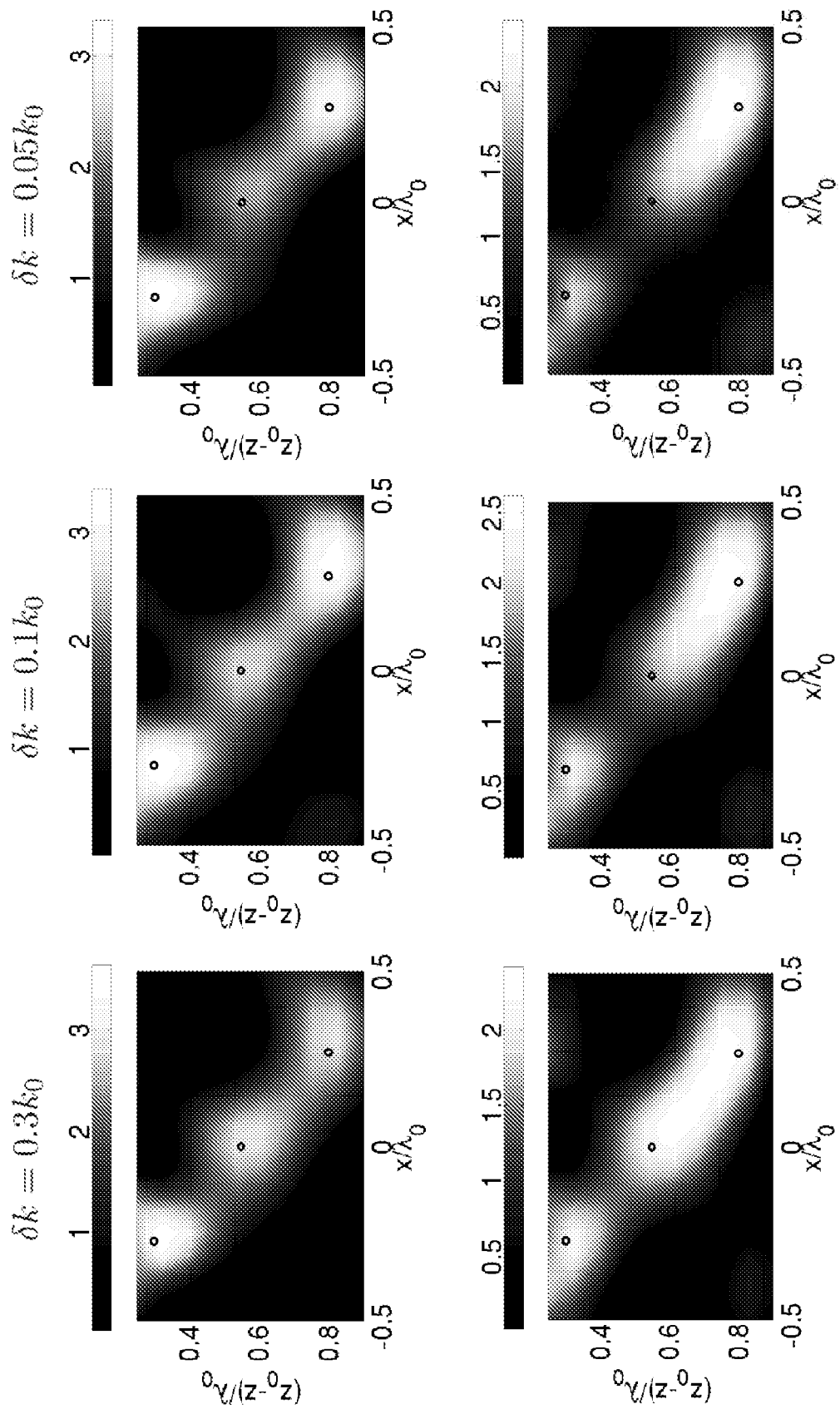

Three different bandwidths were considered, each with different numbers of incident angles. From the simulated forward data, the reconstructions were computed with inversion procedures described above, with Tikhonov regularization. The regularization parameters are decided by experiment. The reconstructed images are shown in FIGS. 5(a-j). In these images, locations of original point scatterers are indicated by circles for comparison. From these reconstructions, sub-wavelength resolution in the transverse and depth directions may be observed. It is also seen that the reconstruction improves with increased bandwidth and increased number of angles of incidence. These two parameters jointly produce an effective total bandwidth not achievable with single-angle spectroscopic illumination, yet the total number of angles of incidence is largely reduced compared to a multiple-angle monochromatic configurations described in Sun et al. (2006) and Sun et al. (2007). The more spectroscopic bandwidth is available in the illumination source, the fewer the number of angles that is needed for the same resolvability.

Figure 6A:
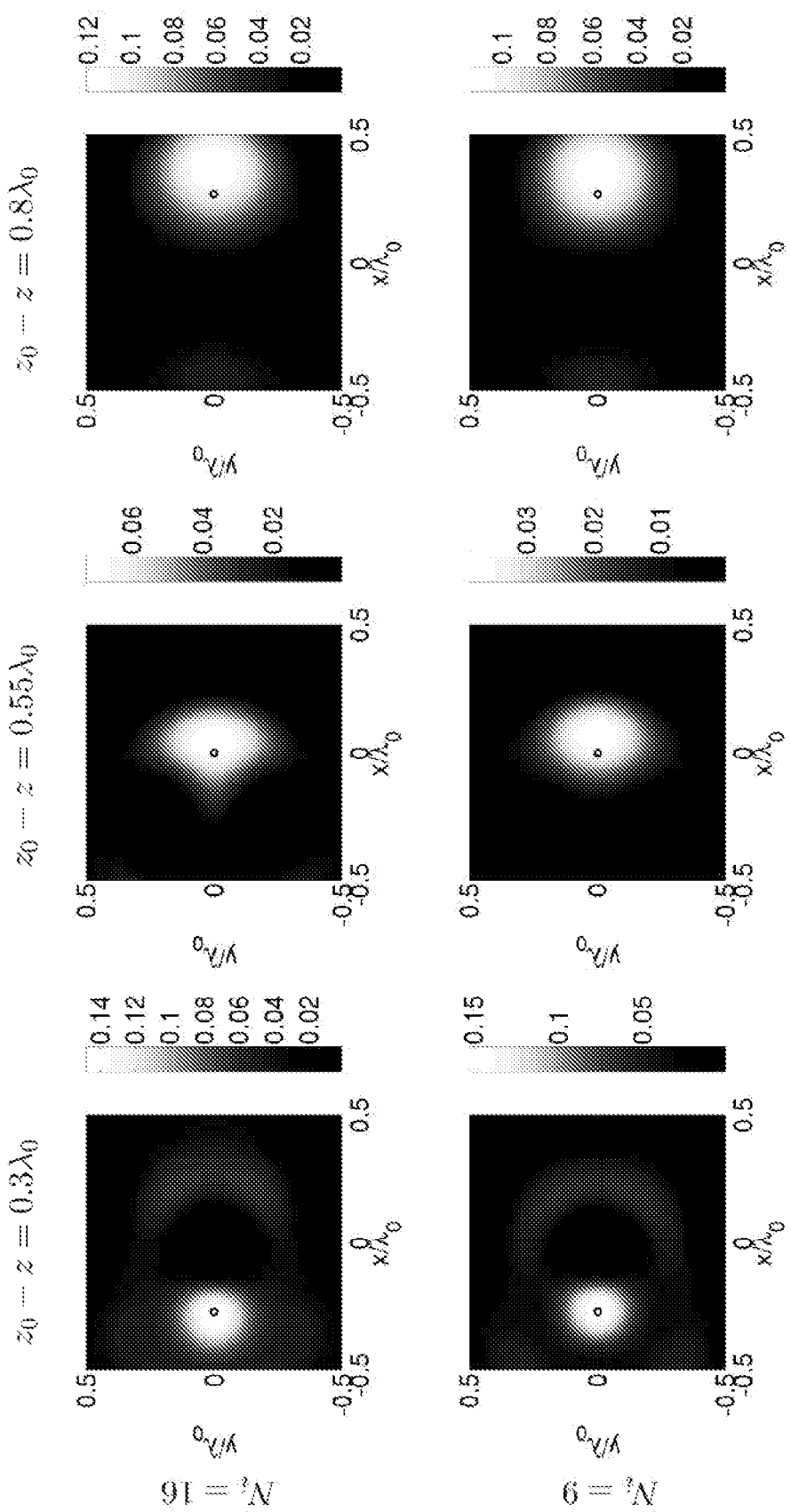
FIGS. 6(*a-b*) show individually reconstructed layers of the sample, with an illumination scheme the same as in FIGS. 5(*a-b*), and a bandwidth of illumination of $\delta k=0.1 k_0$, where $z_0-z$ is the distance from the measurement plane to the reconstructed layer.
Figure 6B:
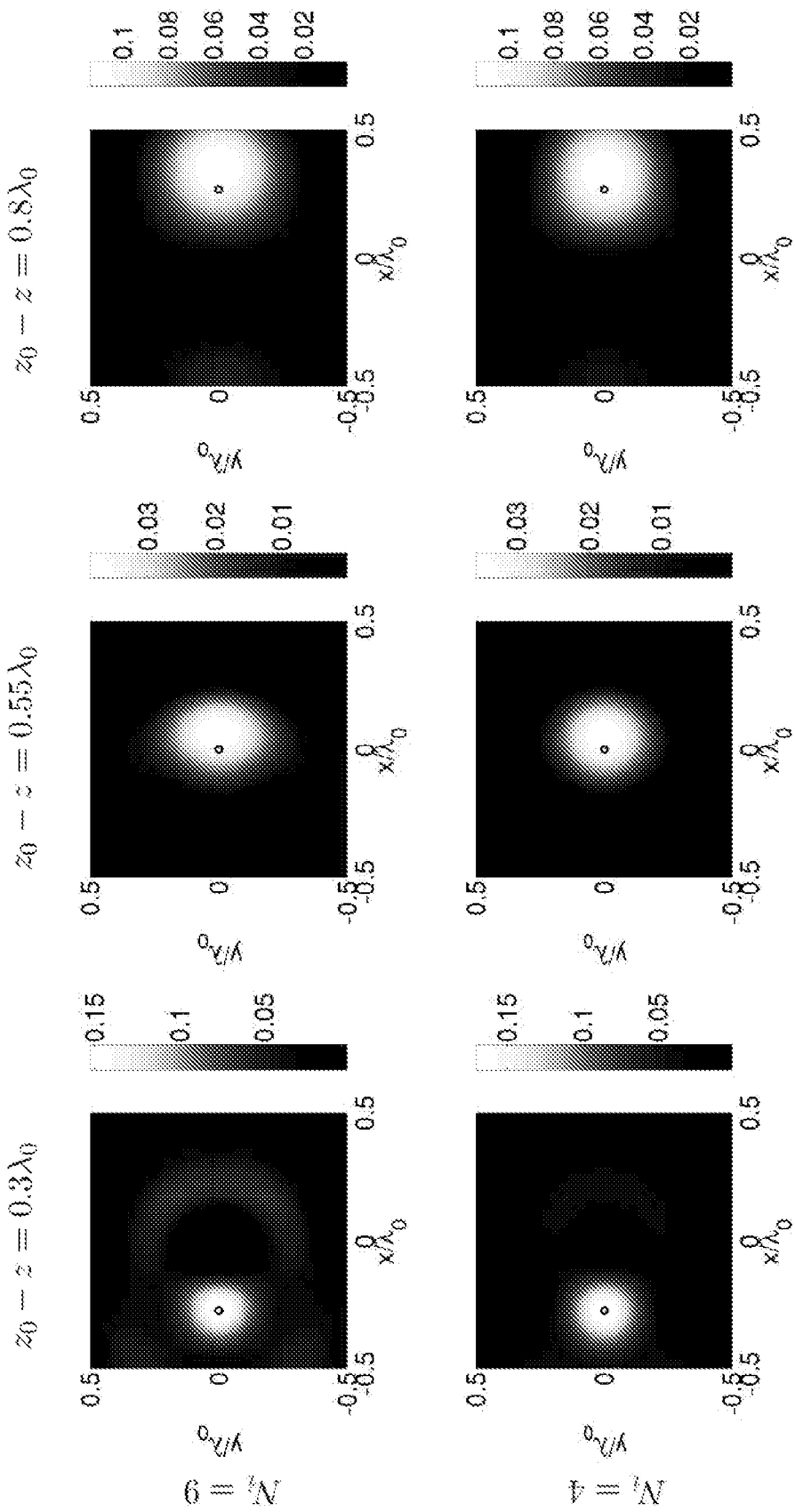

In some cases, only certain horizontal slices of the reconstruction are needed, and relationship between these slices is not important. Hence, regularizations may be adjusted to optimize a given layer. In FIGS. 6(a-b), the reconstructions are shown in the three horizontal layers where the point scatterers are located. These reconstructions are produced individually, with different regularization for different layers. As a result, different layers are not comparable, in contrast to those shown in FIGS. 5(a-b). Reconstruction thus produced are less noisy and quality is less sensitive to number of illumination angles and bandwidth compared to the previous case. As a tradeoff, these images may not be regarded as a tomography of the sample, they should rather be viewed as a computational re-focusing of the scattered near field for a fixed depth in the sample.

It becomes apparent when field polarization and physical boundary are taken into account in the analysis of spectroscopic NSOT that mechanical variation of the illumination or measurement devices may advantageously be reduced, thus reducing both experimental complexity as well as mechanical noise. Moreover, it is seen that multiple-angle and broadband illumination may be used to produce an effective bandwidth much larger than a typical broadband light source.

Embodiments of the invention heretofore described are intended to be merely exemplary and numerous variations and modifications will be apparent to those skilled in the art. More particularly, and as an example, while the foregoing description has been provided under an assumption that the sample is nondispersive, the results presented are readily generalized, within the scope of the invention, to encompass cases where the sample has a spatially-invariant, well-characterized spectral response.

The invention may be embodied in any number of instrument modalities, such as illuminating-probe, collecting-probe, multiple probes, etc., all within the scope of the invention. Moreover, it is to be understood that the "aperture" or "probe" may be more complex than a single point, and that the extension to a more complex analysis is within the scope of the present invention. Furthermore, in alternative embodiments, the disclosed methods of near-field imaging may be implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product). All such variations and modifications are within the scope of the present invention as defined in any appended claims.

What is claimed is:

1. A method for imaging an object, the method comprising:
   a. illuminating the object with an illuminating electromagnetic wave via an illumination path, the illuminating electromagnetic wave being characterized by a spectrum of illuminating wavevectors;
   b. detecting, via a collection path, electromagnetic waves scattered by the object and incident upon a detector, the detected electromagnetic waves being characterized by a spectrum of detected wavevectors; and
   c. varying the magnitude of at least one of the illuminating wavevectors and detected wavevectors in such a manner as to provide information regarding a scattering characteristic of the object, wherein an aperture, disposed within at least one of the illuminating path and collecting path, has a characterizing dimension equal to or smaller than an instantaneous characterizing wavelength of the illuminating electromagnetic wave.

2. A method in accordance with claim 1, wherein the information provided regarding a scattering characteristic is in a direction along the illuminating path.

3. A method in accordance with claim 1, wherein the step of detecting includes disposing a detector in a far field.

4. A method in accordance with claim 1, wherein the aperture includes a tip.

5. A method in accordance with claim 1, wherein the illumination path, collecting path, and detector comprise an imaging system, the method further comprising:
   d. applying a forward model of the imaging system in a manner as to derive a three-dimensional scattering model; and
   e. inverting a function of the detected data in terms of the forward model to obtain a three-dimensional reconstruction of the object.

6. A method in accordance with claim 5, wherein the forward model is expressed in terms of a block-diagonalized forward integral equation.

7. A method in accordance with claim 1, wherein the step of illuminating the object includes illumination by means of a broadband source.

8. A method in accordance with claim 7, wherein the broadband source is a pulsed laser.

9. A method in accordance with claim 1, wherein the step of illuminating the object includes scanning a wavelength of a substantially monochromatic source.

10. A method in accordance with claim 1, further comprising varying observing angles.

11. A method in accordance with claim 1, further comprising:
    scanning the aperture to a plurality of positions in a plane substantially parallel to the surface of the object.

12. A method in accordance with claim 11, wherein scanning the aperture includes scanning a position of a probe tip that is small on a scale of the characterizing wavelength of the illuminating electromagnetic wave.

13. A method in accordance with claim 1, further including a step of spectrally dispersing electromagnetic waves scattered by the object prior to detection by the detector.

14. A method in accordance with claim 1, wherein the step of detecting electromagnetic waves scattered by the object includes detecting a phase of the scattered electromagnetic waves.

15. A computer program product for deriving an image of a physical object, the computer program product comprising a tangible, non-transitory, computer usable medium for use with a computer system and having computer readable program code thereon, the computer usable medium including:

a. tangible, non-transitory program code for use with the computer system for generating a forward scattering model that includes variation of a magnitude of an illuminating wavevector and a corresponding wavelength, and interposition of an aperture in an illuminating path or a collection path, wherein the aperture has a characterizing dimension equal to, or smaller than an instantaneous characterizing wavelength of the illuminating wavevector;

b. tangible, non-transitory program code for receiving a signal based on detection of scattering from the physical object; and c. tangible, non-transitory program code for deriving a scattering characteristic of the physical object based on comparison with the forward scattering model of detected scattering from the object.

16. A computer program product in accordance with claim 15, further comprising:

d. tangible, non-transitory program code for applying a forward model of the imaging system in a manner as to derive a three-dimensional scattering model; and e. tangible, non-transitory program code for inverting a detected data function in terms of the forward model to obtain a three-dimensional reconstruction of the object.

17. An apparatus for imaging a sample in three dimensions, the apparatus comprising:

a. an illumination source for illuminating the sample with an illuminating electromagnetic wave via an illumination path, the illuminating electromagnetic wave being characterized by a spectrum of illuminating wavevectors;

b. a detector for detecting electromagnetic waves scattered by the sample along a collection path, the scattered electromagnetic waves being characterized by a spectrum of detected wavevectors, wherein the illuminating path, collection path, and detector comprise an imaging system;

c. an aperture having a characterizing dimension equal to or smaller than an instantaneous characterizing wavelength of any of the illuminating wavevectors or detected wavevectors, the aperture being disposed within at least one of the illuminating path and the collection path and having a relative position with respect to the sample;

d. a scanner for varying the relative position of the sample and the aperture; and e. a processor adapted to control the scanner, apply a forward model of the imaging system to derive a three-dimensional scattering model, and invert a detected data function in terms of the forward model to obtain a three-dimensional reconstruction of the sample.

18. An apparatus in accordance with claim 17, wherein the illumination source is a broadband source.

19. An apparatus in accordance with claim 18, wherein the illumination source comprises a laser, the laser being tunable in wavelength.

20. An apparatus in accordance with claim 17, wherein the processor is further adapted to control the illumination source.

\* \* \* \* \*